United States Patent
Sano et al.

(10) Patent No.: US 7,119,305 B2
(45) Date of Patent: Oct. 10, 2006

(54) TUBE CONNECTING APPARATUS

(75) Inventors: Hiroaki Sano, Nakakoma-gun (JP); Masaru Nagashimada, Nakakoma-gun (JP); Shinji Ishida, Nakakoma-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/532,788

(22) PCT Filed: Sep. 17, 2003

(86) PCT No.: PCT/JP03/11860

§ 371 (c)(1),
(2), (4) Date: May 20, 2000

(87) PCT Pub. No.: WO2004/039563

PCT Pub. Date: May 13, 2004

(65) Prior Publication Data

US 2006/0054613 A1    Mar. 16, 2006

(30) Foreign Application Priority Data

Nov. 1, 2002    (JP) ............................. 2002-319497

(51) Int. Cl.
*H05B 1/00*    (2006.01)
(52) U.S. Cl. .................................... 219/243; 156/304.2
(58) Field of Classification Search ............... 219/243, 219/535, 544, 521, 385, 494; 156/304.2, 156/515
See application file for complete search history.

(56) References Cited

U.S. PATENT DOCUMENTS

| | | | | |
|---|---|---|---|---|
| 5,554,253 A | * | 9/1996 | Watanabe | ................... 156/503 |
| 5,802,689 A | * | 9/1998 | Sano | ........................... 29/33 T |
| 6,705,372 B1 | * | 3/2004 | Sano et al. | .................. 156/503 |
| 6,913,056 B1 | * | 7/2005 | Landherr et al. | ............ 156/378 |

FOREIGN PATENT DOCUMENTS

| | | |
|---|---|---|
| EP | 0 101 315 A2 | 2/1984 |
| EP | 0 105 587 A1 | 4/1984 |
| EP | 0 778 123 A2 | 6/1997 |
| JP | A 6-78971 | 3/1994 |
| JP | A 6-91009 | 4/1994 |
| JP | A 6-91010 | 4/1994 |
| JP | A 11-178889 | 7/1999 |

* cited by examiner

*Primary Examiner*—Robin Evans
*Assistant Examiner*—Vinod Patel
(74) *Attorney, Agent, or Firm*—Oliff & Berridge, PLC

(57) ABSTRACT

The present invention has a purpose of providing a tube connecting apparatus capable of stably, accurately executing control of wafer temperature even when connecting of tubes is conducted continuously. A tube connecting apparatus (1) includes a heater (70) for heating a wafer holder (5a), a thermister (71) which detects the temperature of the wafer holder (5a), a heater heating control device (69) which controls the heater (70) based on output of the thermister (71), and a wafer heating control device (68) which performs heating control of a wafer (6) through constant power control. Before the start of heating the wafer (6) by the wafer heating control device (68), the control of the heater (70) is performed by the heater heating control device (69) for temperature control so that the wafer holder (5a) is heated to a fixed temperature (about 65° C.).

10 Claims, 16 Drawing Sheets

TUBE CONNECTING APPARATUS

TECHNICAL FIELD

The present invention relates to a tube connecting apparatus for connecting tubes in sterile condition and more particularly to a tube connecting apparatus capable of stabilizing a temperature of a wafer during cutting and connecting of tubes.

BACKGROUND ART

During connection of tubes of a blood-collecting bag and a blood-component bag in a blood transfusion system, replacement of a waste liquid bag with a dialysate bag, and other operations in continuous ambulatory peritoneal dialysis (CAPD), it is necessary to connect (join) tubes under a sterilized condition. One of apparatuses for aseptically connecting tubes is disclosed for example in Japanese unexamined patent publication No. H6(1994)-78971. An apparatus disclosed in this publication No. H6(1994)-78971 includes a first clamp and a second clamp which hold at least two flexible tubes in parallel relation, a cutting means for cutting the flexible tubes between the first and second clamps, and a moving means for moving at least one of the first and second clamps so that the end portions to be connected of the flexible tubes cut with the cutting means are brought into close contact with each other. The cutting means includes a wafer for melting and cutting the flexible tubes, a constant-voltage source for heating the wafer, a wafer temperature detecting means, and a wafer heating control means. The wafer heating control means has a signal output section for outputting a pulse width modulation calculated based on output of the wafer-temperature detecting means and is arranged to control the temperature of the wafer according to the pulse width modulation signal.

In this apparatus, the wafer heating control means outputs the pulse width modulation signal calculated based on the output of the wafer-temperature detecting means, thereby controlling the temperature of the wafer. In other words, the control of the wafer temperature is performed through feedback control based on the output of the wafer-temperature detecting means.

Another method of controlling the wafer temperature is disclosed for example in Japanese unexamined patent publication No. S59(1984)-64034. The method disclosed in this publication No. S59(1984)-64034 is a method in which electric power for heating a wafer is controlled through constant power control while referring to a temperature at a start of heating up the wafer.

The apparatus disclosed in the above publication '971, however, may cause unstable temperature measurement according to a contact state of the wafer-temperature detecting means with the wafer. Due to long-term use, plasticizer or the like contained in the tubes is likely to adhere to a surface of the wafer-temperature detecting means. Thus the wafer-temperature detecting means may inaccurately measure the temperature of the wafer. Unstable, inaccurate temperature measurement by the wafer-temperature detecting means would lead to unstable, inaccurate control of the wafer temperature. The temperature measurement would become unstable depending on the contact state of the wafer-temperature detecting means with the wafer as mentioned above. For enabling accurate temperature measurement, an adjustment work is performed in mounting the wafer-temperature detecting means. Such adjustment would take much time.

In the wafer-temperature control method disclosed in the publication '034, on the other hand, the wafer temperature is referred to only at the start of wafer heating-up. Thus, when constant electric power is applied to the wafer, a final temperature of the heated wafer may vary from wafer to wafer. In other words, the wafer temperature could not be controlled stably. This is because the presence/absence and direction of thermal flux to each wafer vary due to a difference in elapsed time from a previous connecting operation and other factors. In successive tube connecting operations, particularly, the final temperature of the heated wafer tends to vary.

DISCLOSURE OF INVENTION

The present invention has a purpose to provide a tube connecting apparatus capable of stably, accurately executing wafer temperature control even when tube connecting operations are conducted successively.

A tube connecting apparatus according to the invention made to achieve the above purpose is characterized in a tube connecting apparatus for connecting flexible tubes in sterile condition, the apparatus comprising: a first clamp and a second clamp which hold at least two flexible tubes; cutting means for cutting the flexible tubes between the first and second clamps; and moving means which moves at least one of the first clamp and the second clamp so that the end portions to be connected of the flexible tubes cut by the cutting means contact closely with each other; wherein the cutting means comprises: a wafer for melting and cutting the flexible tubes; a wafer holder which holds the wafer; heating means for heating the wafer holder; temperature detecting means for detecting the temperature of the wafer holder; and heating control means for controlling the heating means; and the heating control means controls the heating means so that the wafer holder is heated to a predetermined temperature based on output of the temperature detecting means.

A tube connecting apparatus according to another aspect of the invention is characterized in a tube connecting apparatus for connecting flexible tubes in sterile condition, the apparatus comprising: a first clamp and a second clamp which hold at least two flexible tubes; cutting means for cutting the flexible tubes between the first and second clamps; and moving means which moves at least one of the first clamp and the second clamp so that the end portions to be connected of the flexible tubes cut by the cutting means make close contact with each other; wherein the cutting means comprises: a wafer for melting and cutting the flexible tubes; wafer heating means for heating the wafer; wafer heating control means for controlling the wafer heating means; a wafer holder which holds the wafer; heating means for heating the wafer holder; temperature detecting means for detecting the temperature of the wafer holder; and heating control means for controlling the heating means; and the heating control means controls the heating means before the wafer is heated by the wafer heating means so that the wafer holder is heated to a predetermined temperature based on output of the temperature detecting means.

In the above tube connecting apparatus, the predetermined temperature is preferably within 50° C. to 80° C., more preferably, within 60° C. to 70° C.

In the above tube connecting apparatus, preferably, the heating control means the heating control means controls the heating means so that the temperature of the wafer holder is lower than the predetermined temperature when a subsequent tube connecting operation is not conducted for a predetermined period of time after a tube connecting operation. In the above tube connecting apparatus, preferably, the temperature detecting means includes a thermister and a temperature reading circuit which measures the temperature of the wafer holder based on an output signal of the thermister.

In the above tube connecting apparatus, preferably, the wafer heating control means controls the wafer heating means through constant power control based on a level of electric current and voltage of the wafer.

In the above tube connecting apparatus, preferably, the wafer heating control means controls the wafer heating means through pulse width modulation control based on a difference between an amount of electric power consumption of the wafer calculated based on the levels of electric current and voltage of the wafer and an amount of target electric power set in advance.

BEST MODE FOR CARRYING OUT THE INVENTION

Figure 1:
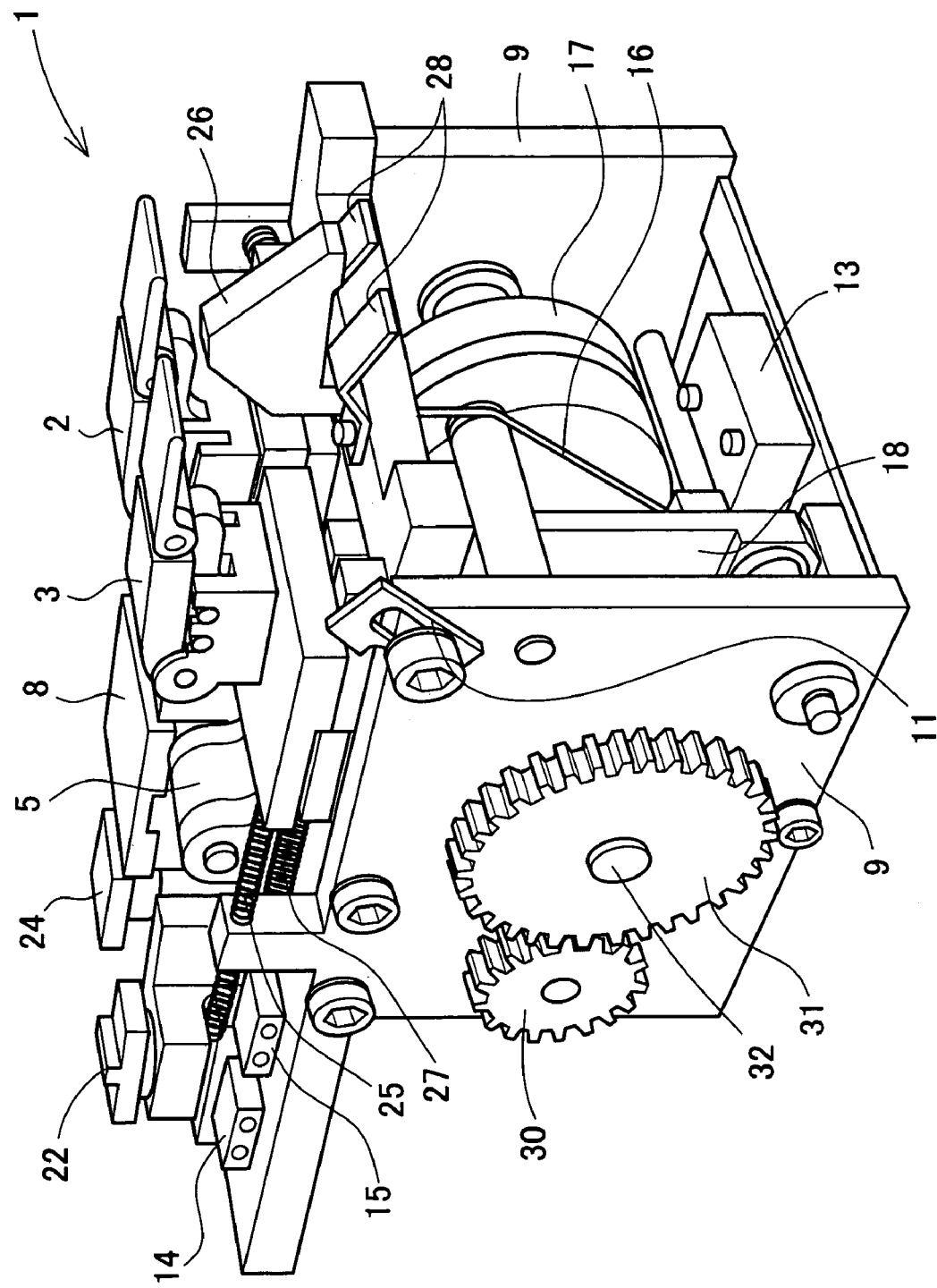
FIG. 1 is a perspective view showing a tube connecting apparatus in a preferred embodiment.
Figure 2:
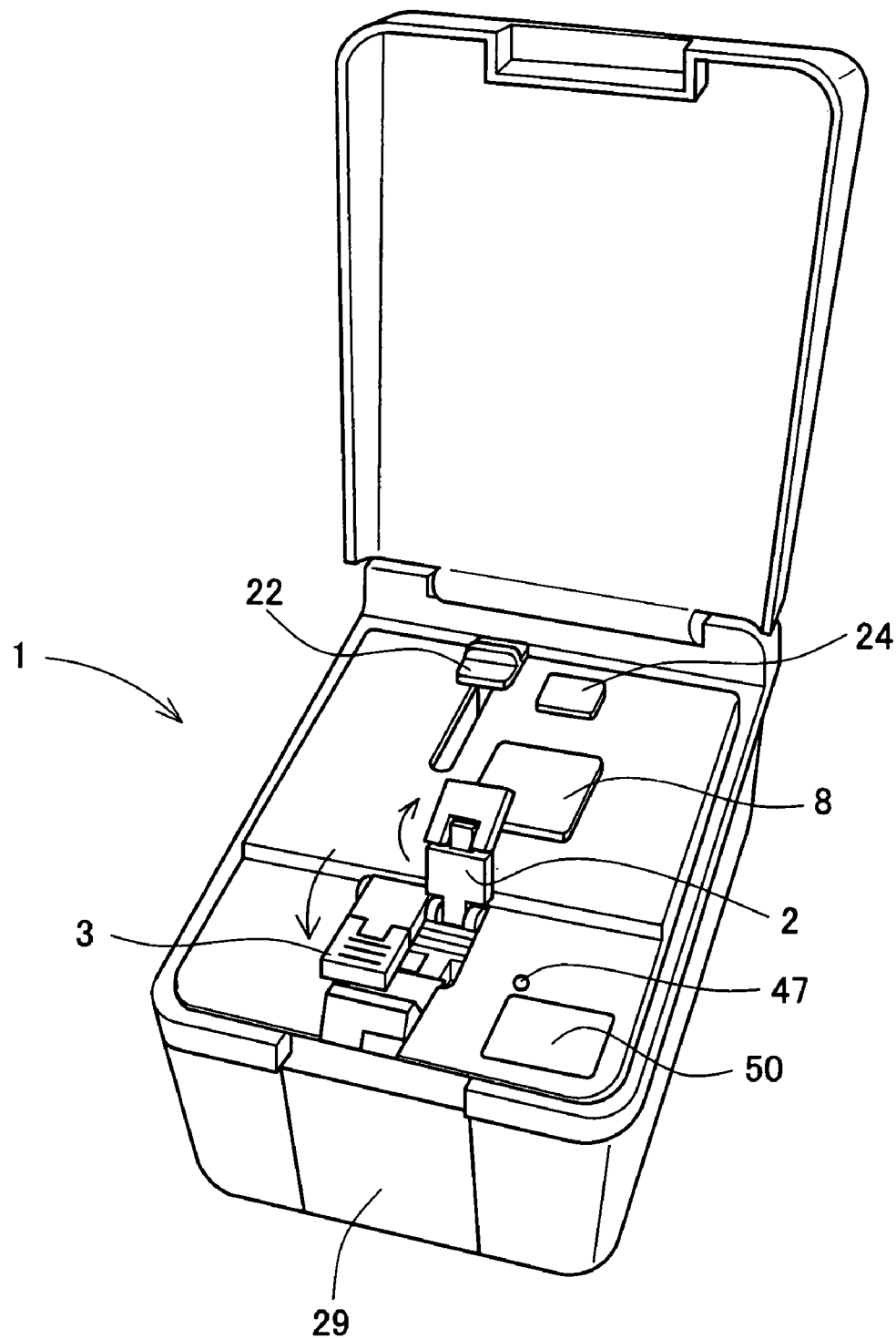
FIG. 2 is a perspective view showing a state where the tube connecting apparatus in the embodiment is housed in a case.
Figure 3:
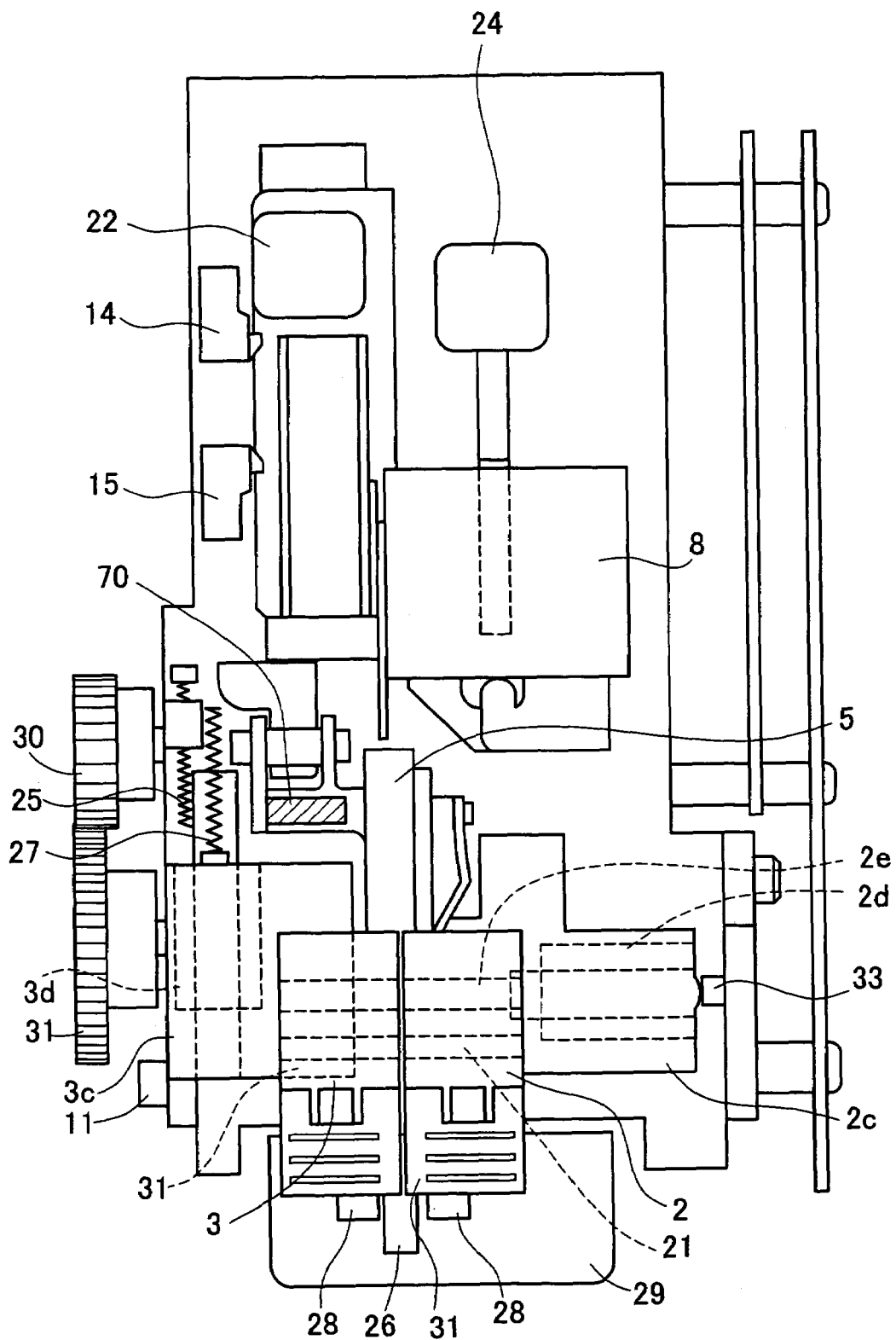
FIG. 3 is a plan view of the tube connecting apparatus in the embodiment.
Figure 4:
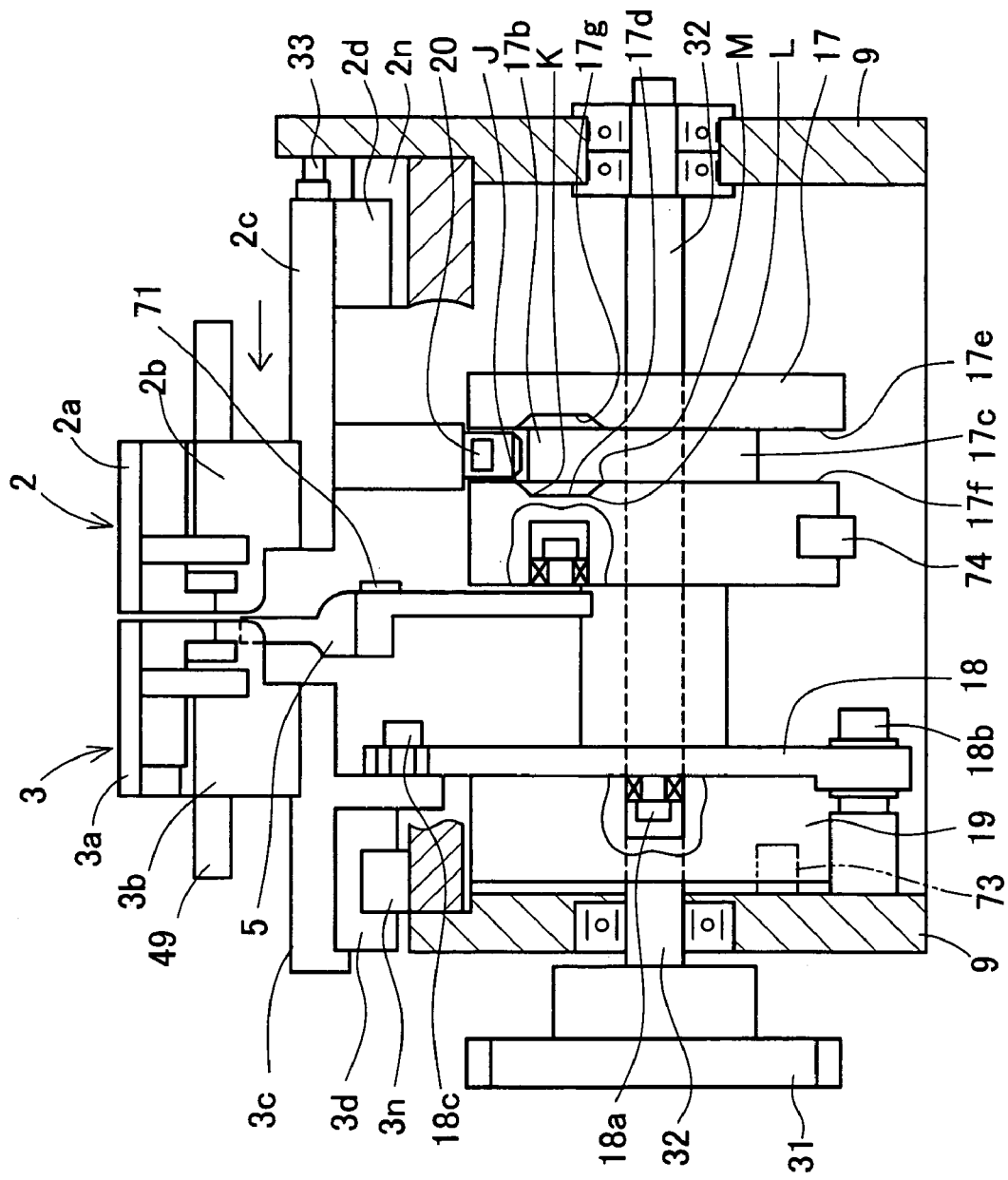
FIG. 4 is an explanatory view for operations of a first and second clamps and a cutting device.

A detailed description of a preferred embodiment of a tube connecting apparatus embodying the present invention will now be given referring to the accompanying drawings. The tube connecting apparatus in the embodiment is suitable for use in successive tube connecting operations such as tube connecting of a blood collecting bag and a blood component bag in a blood transfusion system. A schematic structure of this tube connecting apparatus is shown in FIGS. 1 through 4. FIG. 1 is a perspective view of the tube connecting apparatus; FIG. 2 is a perspective view showing a state where the tube connecting apparatus housed in a case; FIG. 3 is a plan view of the tube connecting apparatus, and FIG. 4 is an explanatory view for operations of a first clamp, a second clamp, and a cutting device.

A tube connecting apparatus 1 includes a first clamp 3 and a second clamp 2 which hold at least two flexible tubes in parallel relation. The apparatus further includes a gear 30 which is rotated by activation of a motor, a gear 31 which is rotated by the rotation of the gear 30, a shaft 32 which is rotated by the rotation of the gear 31, a frame 9 to which both ends of the shaft is rotatably fixed, a wobble preventing member 11 for preventing a wobble of the first clamp 3 at a home position, microswitches 13, 14, and 15, a driving arm 18 for moving the first clamp 3, a cam 19 for moving the first clamp 3, a cutting device 5, a cam 17 for moving the cutting device 5 and the second clamp 2, a pressing member 33 which presses the second clamp 2 against the first clamp 3, a restriction member 25 which restricts a backward position of the first clamp 3, a spring member 27 for preventing the wobble of the first clamp 3, a wafer replacement lever 22, a wafer cartridge 8, a wafer cartridge replacement lever 24, a holding member 28 which grasps a used-wafer storage box, a guiding member 26 for guiding used wafers to a storage box, a used-wafer storage box 29, and a panel 50.

This tube connecting apparatus 1 is provided with a first clamp 3 moving mechanism for moving the first clamp 3 so that the end portions to be connected of flexible tubes 48 and 49 cut by the cutting device 5 face each other, a cutting device driving mechanism for moving the cutting device 5 toward the tubes (upward) and then moving it away from the tubes (downward) after cutting, and a second clamp moving mechanism for moving the second clamp 2 in a direction closer to or away from the first clamp 3. The cutting device driving mechanism is arranged to move the cutting device 5 upward and perpendicular to the axes of two tubes and move it downward after cutting. The first clamp moving mechanism is arranged to move the first clamp 3 in parallel relation and in a perpendicular direction (more specifically, backward) to the axes of two tubes after the cutting. The second clamp moving mechanism is arranged to slightly move the second clamp 2 in horizontal relation and in a parallel direction to the axes of two tubes to come close to the first clamp.

Figure 5:
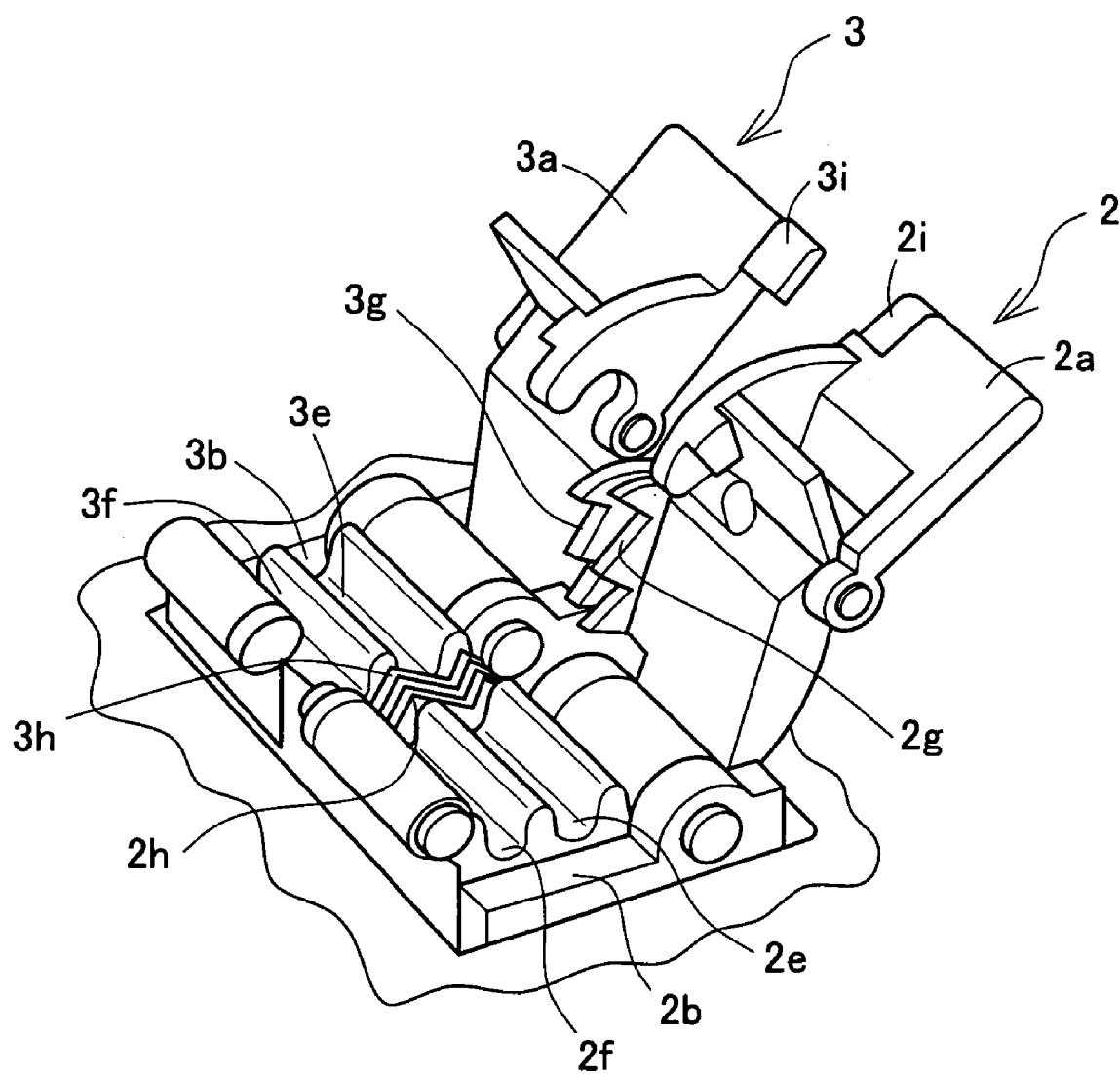
FIG. 5 is a perspective view showing structures of the first and second clamps.

The first and second clamps 3 and 2 will be explained below with reference to FIG. 5. FIG. 5 is a perspective view showing a structure of the first and second clamps. Firstly, the first clamp is explained. The first clamp 3, as shown in FIG. 5, includes a base 3b, a cover 3a rotatably attached to this base 3b, and a clamp mounting base 3c on which the base 3b is mounted. This clamp mounting base 3c is fixed on a linear table. The linear table is constructed of a movable block 3d fixed on a bottom surface of the clamp mounting base 3c and a rail member 3n placed under the movable block 3d (see FIG. 4). With this linear table, the first clamp 3 is moved straight in a perpendicular direction to the axes of the tubes 48 and 49 to be connected, in other words, so that the end portions to be connected of the cut flexible tubes face each other. Accordingly, in the tube connecting apparatus 1, the first clamp moving mechanism is constructed of the above mentioned linear table, motor, gear 30, gear 31, shaft 32, driving arm 18, and cam 19.

This tube connecting apparatus 1 is provided, as shown in FIGS. 1 and 3, with a spring member 27 which connects the back of the first clamp mounting base 3c with a frame of the tube connecting apparatus 1, so that the first clamp 3 is always stretched backward. This reduces a wobble of the first clamp 3 (correctly, the first clamp mounting base 3c). As shown in FIGS. 1 and 3, further, the preventing member 11 for preventing the wobble of the first clamp 3 is fixed to a side of the frame 9 at a tube setting position of the first clamp 3 (i.e., at a position of the first clamp 3 moved most frontward). Accordingly, at the tube setting position, the first clamp 3 is in a backward stretched state by the spring member 27, that is, with no wobble on the backside, and is held against movement frontward than the position by the wobble preventing member 11. The first clamp 3 is thus arranged not to wobble at the tube setting position. The tube connecting apparatus 1 is further provided, as shown in FIGS. 1 and 3, with the restriction member 25 for restricting the maximum backward movement position of the first clamp 3 (correctly, the first clamp mounting base 3c).

Secondly, the second clamp is explained. The second clamp 2, as shown in FIG. 5, includes a base 2b, a cover 2a rotatably attached to the base 2b, and a clamp mounting base 2c on which the base 2b is mounted. This clamp mounting base 2c is fixed on the linear table. The linear table is constructed of a movable block 2d fixed on a bottom surface of the clamp mounting base 2c and a rail member 2n placed under the movable block 2d (see FIG. 4). With this linear table, the second clamp 2 is moved straight in a parallel direction to the tubes 48 and 49 to be connected, in other words, only in a direction to move the second clamp 2 closer to or away from the first clamp 3.

As shown in FIGS. 3 and 4, furthermore, the pressing member 33 is provided between the frame 9 and the clamp mounting base 2c in the tube connecting apparatus 1, thus always pressing the second clamp 2 (correctly, the second mounting base 2c) toward the first clamp 3. As the pressing member 33, a spring member is suitably used. Used as this pressing member 33 is a member which has a pressing force weaker than a repulsive force of the flexible tubes 48 and 49 when they are held in a squeezed condition by the first and second clamps 3 and 2 so that the second clamp 2 is allowed to slightly move in a direction to come away from the first clamp 3 when the clamps hold the flexible tubes. Accordingly, in the tube connecting apparatus 1 in the present embodiment, the second clamp moving mechanism is constructed of the above mentioned linear table, motor, gear 30, gear 31, shaft 32, cam 17, and pressing member 33.

The first clamp 3 and the second clamp 2 are arranged to hold the tubes in obliquely squeezed condition as shown in FIG. 5. The clamps 3 and 2 have the covers 3a and 2a pivotally attached to the bases 3b and 2b which are provided with two slots 3f and 3e and two slots 2f and 2e arranged in parallel for receiving two tubes. Between end faces of the bases 3b and 2b where the slots 3f and 3e and the slots 2f and 2e face each other, sawtooth sealing members 3h and 2h are provided. The covers 3a and 2a are provided with sawtooth sealing members 3g and 2g corresponding in shape to the sealing members 3h and 2h of the above bases 3b and 2b. Each inner surface of the covers 3a and 2a is flat. The covers 3a and 2a have turning cams respectively which are engaged with rollers of the bases 3b and 2b when the covers 3a and 2a are closed. When the covers 3a and 2a are closed, the two tubes are held in obliquely squeezed, sealed condition between the sealing member 3h of the base 3b and the sealing member 3g of the cover 3a and between the sealing member 2h of the base 2b and the sealing member 2g of the cover 2a. The first clamp 3 has a projection 3i projecting toward the second clamp and the second clamp 2 has a recess 2i which receives the projection 3i. The second clamp 2 is constructed so that it cannot be closed unless the first clamp 3 is closed.

Figure 6:
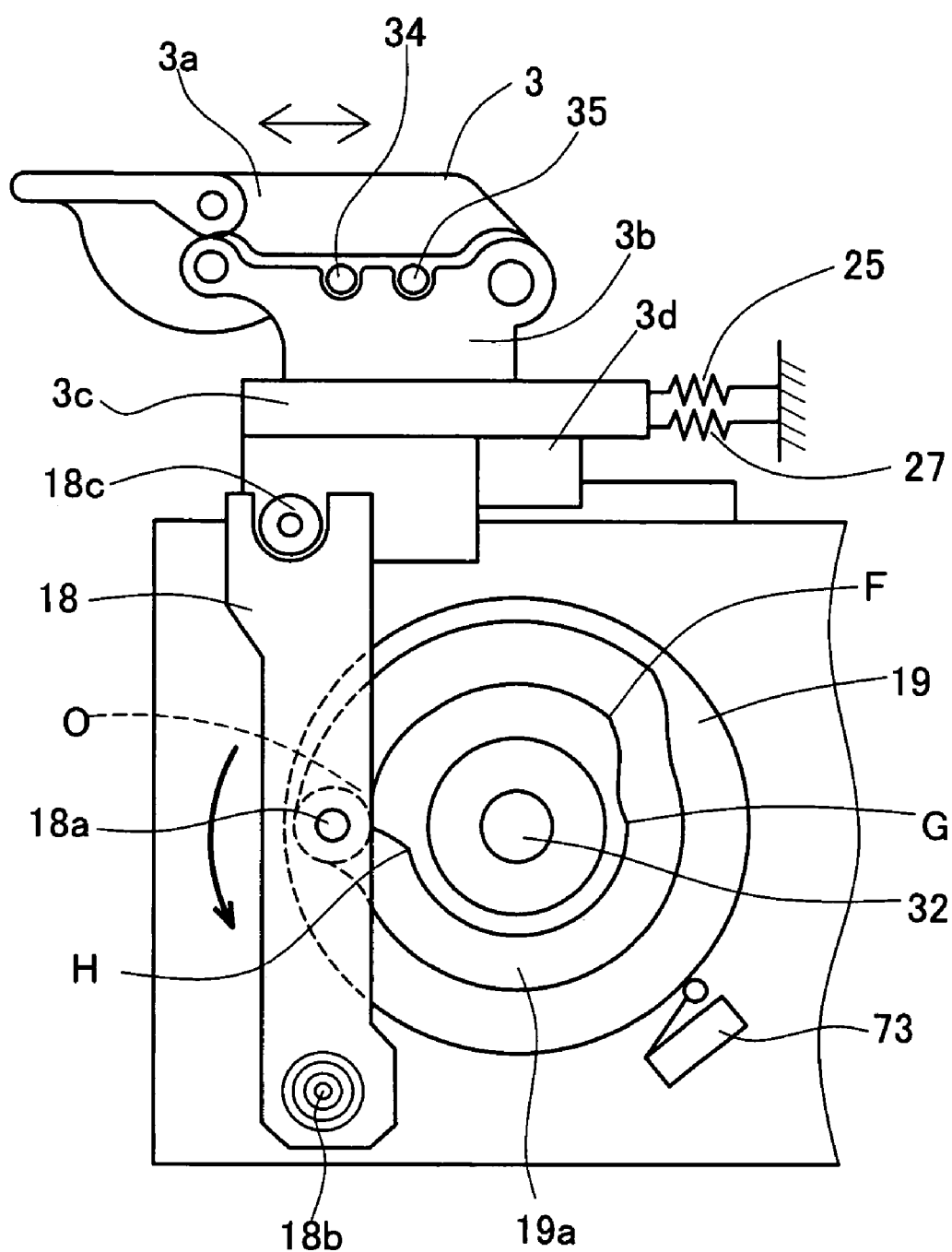
FIG. 6 is an explanatory view for operations of the first clamp.

The tube connecting apparatus 1 includes the gear 30 which is rotated by a motor and the gear 31 which is rotated by the rotation of the gear 30 as shown in FIG. 1, and the two cams 19 and 17 are fixed to the shaft 32 of the gear 31 as shown in FIG. 4. The cams 19 and 17 are rotated by the rotation of the gear 31. Provided on a right side of the cam 19 is a first clamp driving cam groove 19a having s shape shown in FIG. 6. Provided is the first clamp moving arm 18 centrally having a follower 18a which slides in the cam grove 19a of the cam 19. A lower end of the arm 18 is rotatably supported on the frame 9 by a supporting point 18b, while an upper end of the arm 18 is rotatably supported on the clamp mounting base 3c of the first clamp 3 by a supporting point 18c provided on the clamp mounting base 3c. Accordingly, the first clamp 3 is allowed to move along the rail member 3n of the linear table, as shown in FIG. 6, in horizontal relation and in a backward direction perpendicular to the axes of two tubes, as indicated by an arrow, by the rotation of the cam 19 according to the shape of the cam groove 19a. FIG. 6 is an explanatory view for operations of the first clamp.

Figure 7:
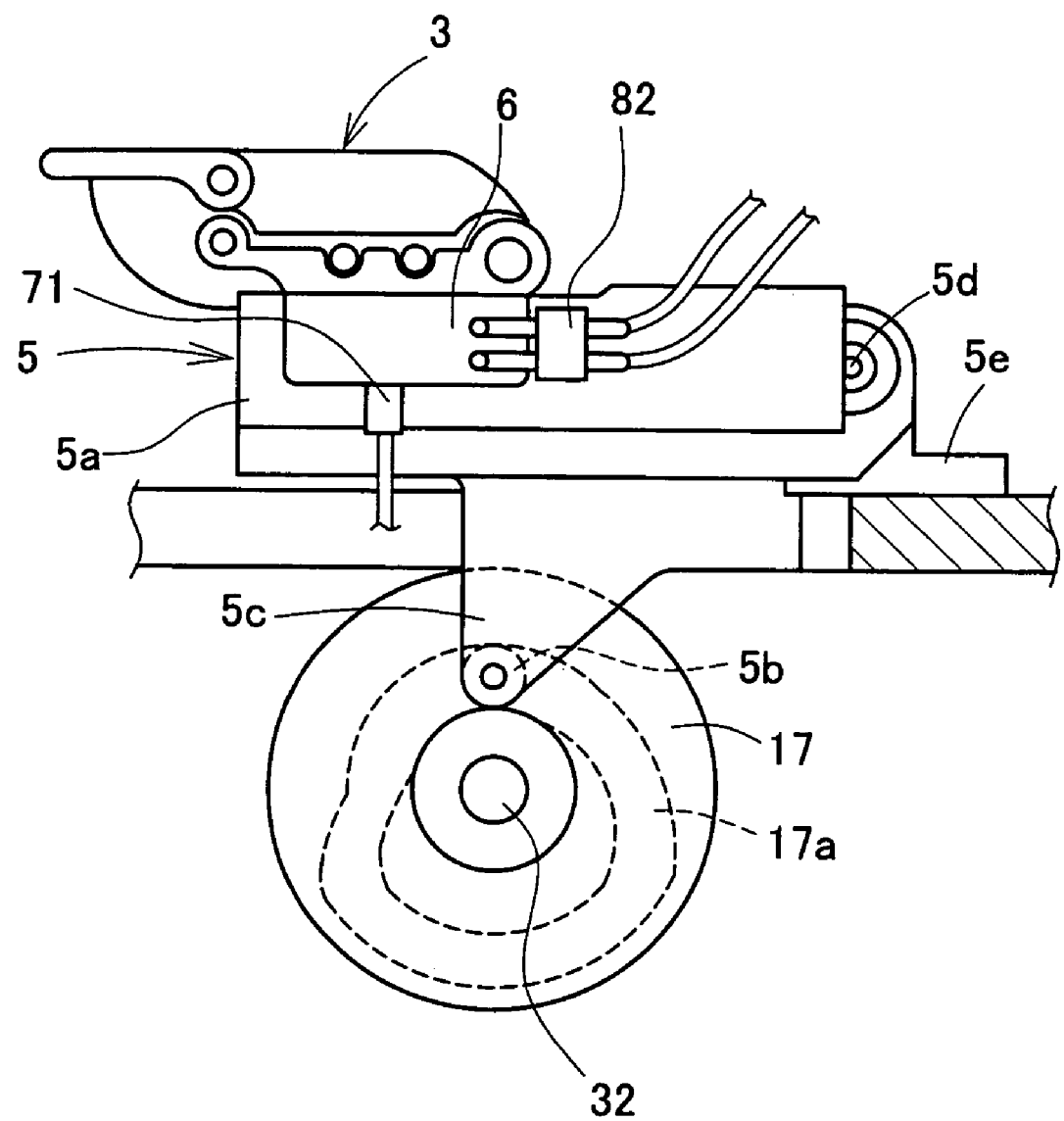
FIG. 7 is a structural view of the cutting device to be used in the tube connecting apparatus in the embodiment.

The cutting device 5, as shown in FIG. 7, includes a wafer holder 5a which holds replaceable wafers, an arm 5c provided under the wafer holder 5a, a follower 5b provided at an end of the arm 5c, a hinge 5d, and a fixing part 5e fixed to the frame 9. The cutting device 5 is pivoted to the frame 9 by the hinge 5. As shown in FIG. 7, furthermore, an electrical contact terminal 82 for heating a wafer is fixed to a right side of the cutting device 5. A thermister 71 for detecting the temperature of the wafer holder 5a is embedded in a bottom of the cutting device 5. FIG. 7 is an explanatory view of the cutting device used in the tube connecting apparatus. A heater 70 is attached on an upper surface of the cutting device 5 as shown in FIG. 3. This heater 70 is used to preheat the wafer holder 5a. Preferably used as the wafer 6 is a wafer having a metal plate bent to have facing ends, an insulating layer formed on an inside face of the metal plate, a resistance element embedded in the insulating layer and without contact with the metal plate, and terminals for energization, provided at both ends of the resistance element.

Figure 8:
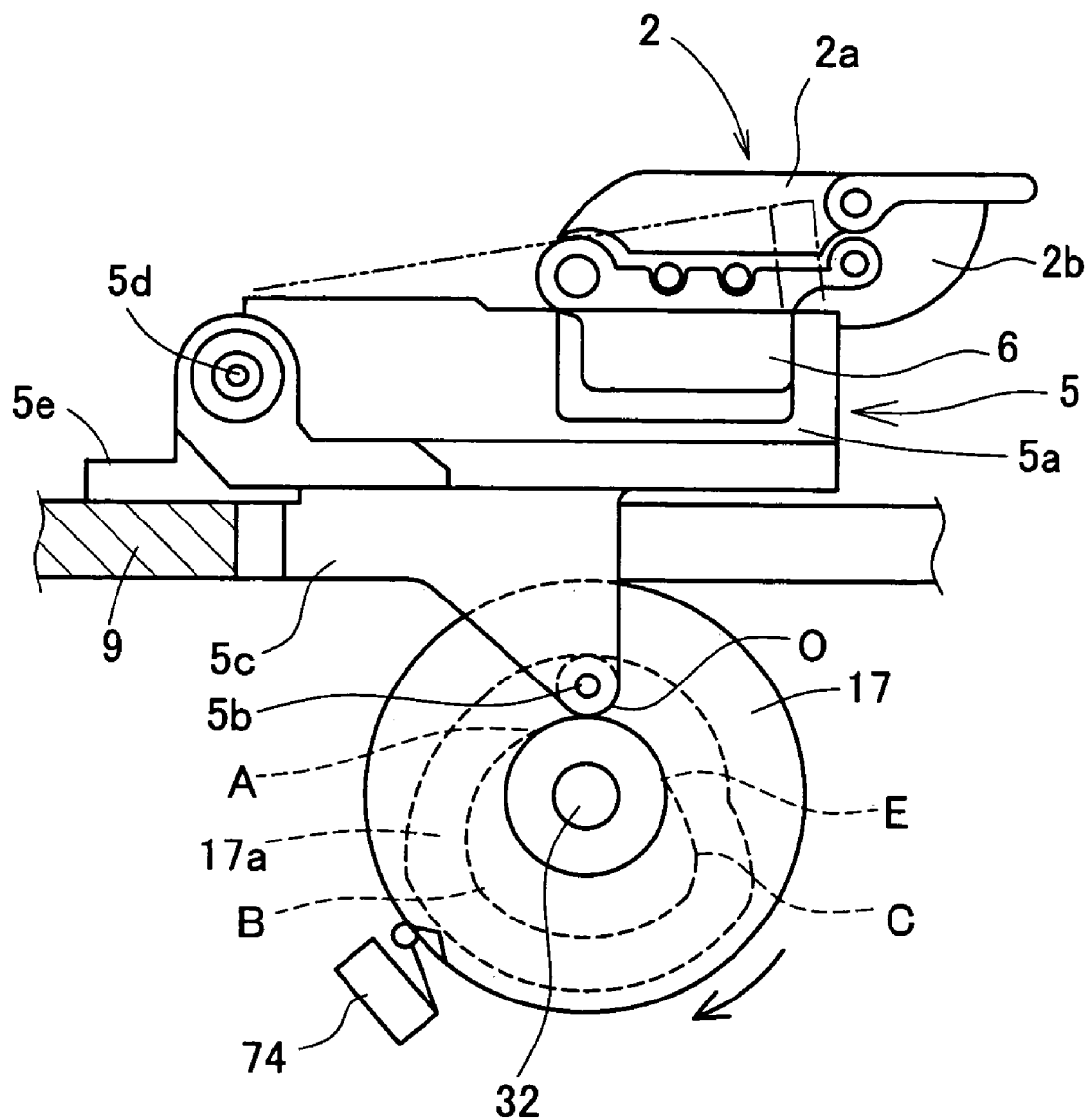
FIG. 8 is an explanatory view for operations of the cutting device.

The cam 17 is formed, on a left side, with a cam groove 17a for driving the cutting device as shown in FIGS. 7 and 8. The follower 5b of the cutting device 5 is placed in the cam groove 17a of the cam 17 and slides in the cam groove 17a along the cam groove shape. Accordingly, as shown in FIG. 8, the rotation of the cam 17 causes the cutting device 5 to move up and down according to the shape of the cam groove 17a, i.e., up and down in a perpendicular and vertical direction to the axes of the two tubes.

The cam 17 is formed, at a center, with a cam groove 17c for driving the second clamp 2 as shown in FIG. 4. The cam groove 17c has a left side face 17f and a right side face 17e whereby the position of the second clamp 2 is controlled. The second clamp mounting base 2c is provided with a protrusion extending downward with a follower 20 at its tip. This follower 20 slides in the cam groove 17c for driving the second clamp 2. As shown in FIG. 7, there is formed a slight clearance between the follower 20 and the side faces of the cam groove 17c. The second clamp mounting base 2c is continuously pressed by the pressing member 33. In a normal state, accordingly, the follower 20 is in contact with the left side face 17*f*, so that a slight clearance is provided between the follower 20 and the right side face 17*e* of the cam groove 17*c*.

When two tubes are held in the first and second clamps 3 and 2, each of the two clamps 3 and 2 seals and holds the two tubes in squeezed condition. Consequently, a repulsive force is developed by the sealing of the tubes. Since the pressing member 33 is a member having a smaller force than the repulsive force caused by the sealing of the tubes, as shown in FIG. 4, the follower 20 is in contact with the right side face 17*e* of the cam groove 17*c* while the clamps 3 and 2 hold the tubes. Thus, a slight clearance is generated between the follower 20 and the left side face 17*f* of the cam groove 17*c*. When the tubes are cut by the above mentioned cutting device 5, however, the repulsive force resulting from the sealing of the tubes is eliminated and therefore the follower 20 is returned to a normal state where the follower 20 makes contact with the left side face 17*f* of the cam groove 17*c*. Accordingly, the slight clearance is generated between the follower 20 and the right side face 17*e* of the cam groove 17*c*. In this way, a slide face of the cam groove with which the follower 20 makes contact is changed with time by the action of the pressing member 33 and the repulsive force of the tubes.

As shown in FIG. 4, a recess 17*d* is formed in the left side face 17*f*. The time when the follower 20 passes through the recess 17*d* is after the cutting of the tubes by the cutting device 5 and therefore the follower 20 is sliding along the left side face 17*f* of the cam groove 17*c*. Then, the follower 20 enters in the recess 17*d*. This makes the second clamp 2 move toward the first clamp 3 by a distance corresponding to the depth of the recess 17*d*, which further ensures the connecting of the tubes.

A recess 17*g* is similarly formed in the right side face 17*e* of the cam groove 17*c*. This recess 17*g* is used for cleaning of each inner surface of the clamps 3 and 2. When the second clamp 2 is pushed toward the spring member 33, the recess 17*g* allows the second clamp 2 to move in a direction to come away from the first clamp 3 until the follower 20 makes contact with the recess 17*g*. This produce a clearance between the first clamp 3 and the second clamp 2. Each inner surface can be cleaned with a cleaning thing, inserted in the clearance, such as a swab dampened with solvent, e.g., alcohol, capable of dissolving a certain degree of a material forming the tubes to be cut.

This recess 17*g* is formed at a position substantially facing to the recess 17*d* of the left side face 17*f* (the portion in which the second clamp 2 is moved in a width direction) as shown in FIG. 4. The time when the follower 20 provided in the protrusion extending downward from the second mounting base 2*c* is inside the recess 17*d* corresponds to the state where the target tubes are connected with each other after the cutting of the tubes. In this state, the second clamp 2 is stopped. The first clamp 3 has already been stopped and is placed at a position out of alignment with the second clamp 2. Specifically, as shown in FIG. 1, the first clamp 3 is moved back than the second clamp 2 and positioned out of alignment with the second clamp 2. In this state, an inside surface of the tip end of the second clamp 2 is slightly exposed and also an inside surface of the tip end of the first clamp 3 is slightly exposed. This makes it easy to clean the exposed inner surfaces of the second clamp 2 and the first clamp 3.

Figure 9:
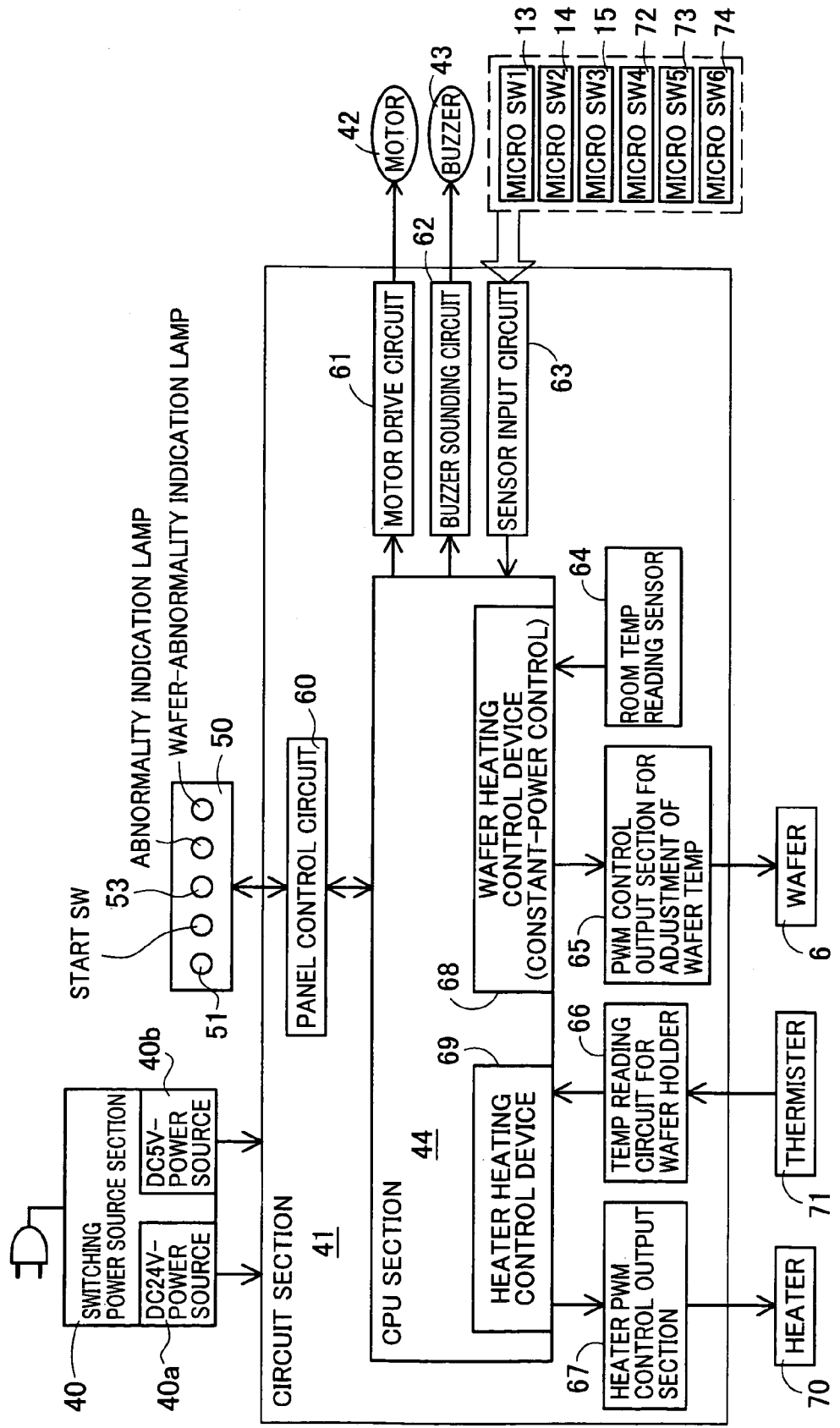
FIG. 9 is a block diagram showing a control system in the tube connecting apparatus in the embodiment.

Next, a control system of the tube connecting apparatus 1 is explained with reference to FIG. 9. FIG. 9 is a block diagram showing the control system of the tube connecting apparatus. The control system in the tube connecting apparatus 1 includes a switching power source section 40, a circuit section 41, and a control circuit for controlling operations of various actuators. The switching power source section 40 includes a DC24V-power source 40*a* for driving various actuators and a DC5V-power source 40*b* serving as a power source for control. The circuit section 41 includes a panel control circuit 60, a motor drive circuit 61, a buzzer sounding circuit 62, a sensor input circuit 63, a room-temperature reading sensor 64, a PWM control output section 65 for controlling a wafer temperature, a temperature reading circuit 66 for a wafer holder, a heater PWM control output section 67, and a CPU section 44 which controls over operations of the above circuits. The CPU section 44 acts as a wafer heating control device 68 and a heater heating control device 69.

Herein, the panel control circuit 60 is a circuit for controlling a displaying operation of the panel 50 provided with a power switch lamp 51 and others. The motor drive circuit 61 is a circuit for controlling a driving operation of a motor 42. The buzzer sounding circuit 62 is a circuit for controlling a sounding operation of a buzzer 43. The sensor input circuit 63 is a circuit for detecting an ON/OFF state of microswitches 13, 14, 16, 72, 73, and 74. The PWM control output section 65 for wafer temperature control is a circuit which outputs a PWM control signal to control heating of the wafer 6. The temperature reading circuit 66 for wafer holder is a circuit to measure a temperature of the wafer holder 5*a* based on a signal from the thermister 71 provided in the cutting device 5. The heater PWM control output section 67 is a circuit which outputs a PWM control signal to control heating of the heater 70 provided in the cutting device 5.

Figure 10:
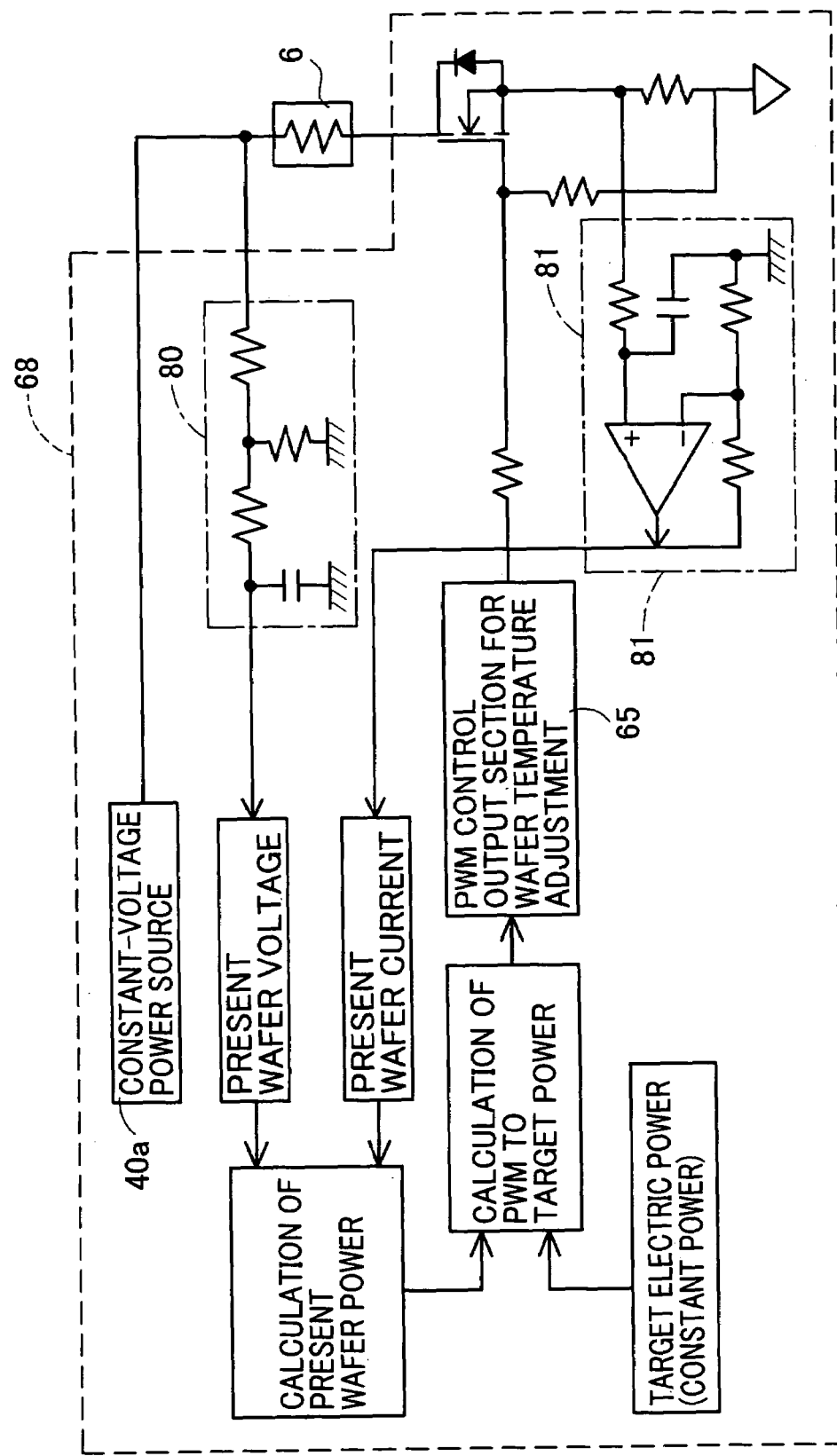
FIG. 10 is a block diagram showing a structure of a wafer heating control device.

Next, the wafer heating control device 68 shown in FIG. 9 is explained in detail, referring to FIG. 10. FIG. 10 is a block diagram showing a structure of the wafer heating control device. Preferably used as the wafer 6 is a wafer having a metal plate bent to have facing ends, an insulating layer formed on an inside face of the metal plate, a resistance element embedded in the insulating layer and without contact with the metal plate, and terminals for energization, provided at both ends of the resistance element. The resistance element generates heat when energized. Therefore the heat of the resistance element generated by energization is transferred to the metal plate, causing the entire wafer to generate heat. A resistance value of the resistance element changes by the heat generation caused by energization. Accordingly, it is impossible to sufficiently control the temperature of the wafer by the regulation of power supply to the wafer through the use of only a constant-voltage source. The tube connecting apparatus 1 in the present embodiment is here provided with the wafer heating control device 68.

This wafer heating control device 68 is used for heating the wafer 6 to a fixed temperature (a temperature at a start of tube cutting, about 320° C.) through constant power control. Thus, there is no need for detecting the temperature of the wafer 6, eliminating the use of the wafer temperature detecting means. An adjustment work in mounting the wafer temperature detecting means is therefore unnecessary and a production efficiency of the tube connecting apparatus can be increased. The wafer heating control device 68 is provided with a wafer-voltage reading circuit 80 for measuring a level of voltage applied to the wafer 6 and a wafer-current reading circuit 81 for measuring a level of electric current flowing in the wafer 6. With these circuits, the wafer heating control device 68 calculates a present wafer electric power based on a present wafer voltage outputted from the wafer-voltage reading circuit 80 and a present wafer current outputted from the wafer-current reading circuit 81 and calculates a pulse width modulation (PWM) signal for controlling the heating of the wafer 6 based on a difference between the calculated electric power and the target electric power. The thus calculated PWM signal is outputted from the PWM control output section 65 for wafer temperature control and a constant-voltage direct-current source 40a is controlled based on the PWM signal. The heating control of the wafer 6 is thus performed.

Figure 12:
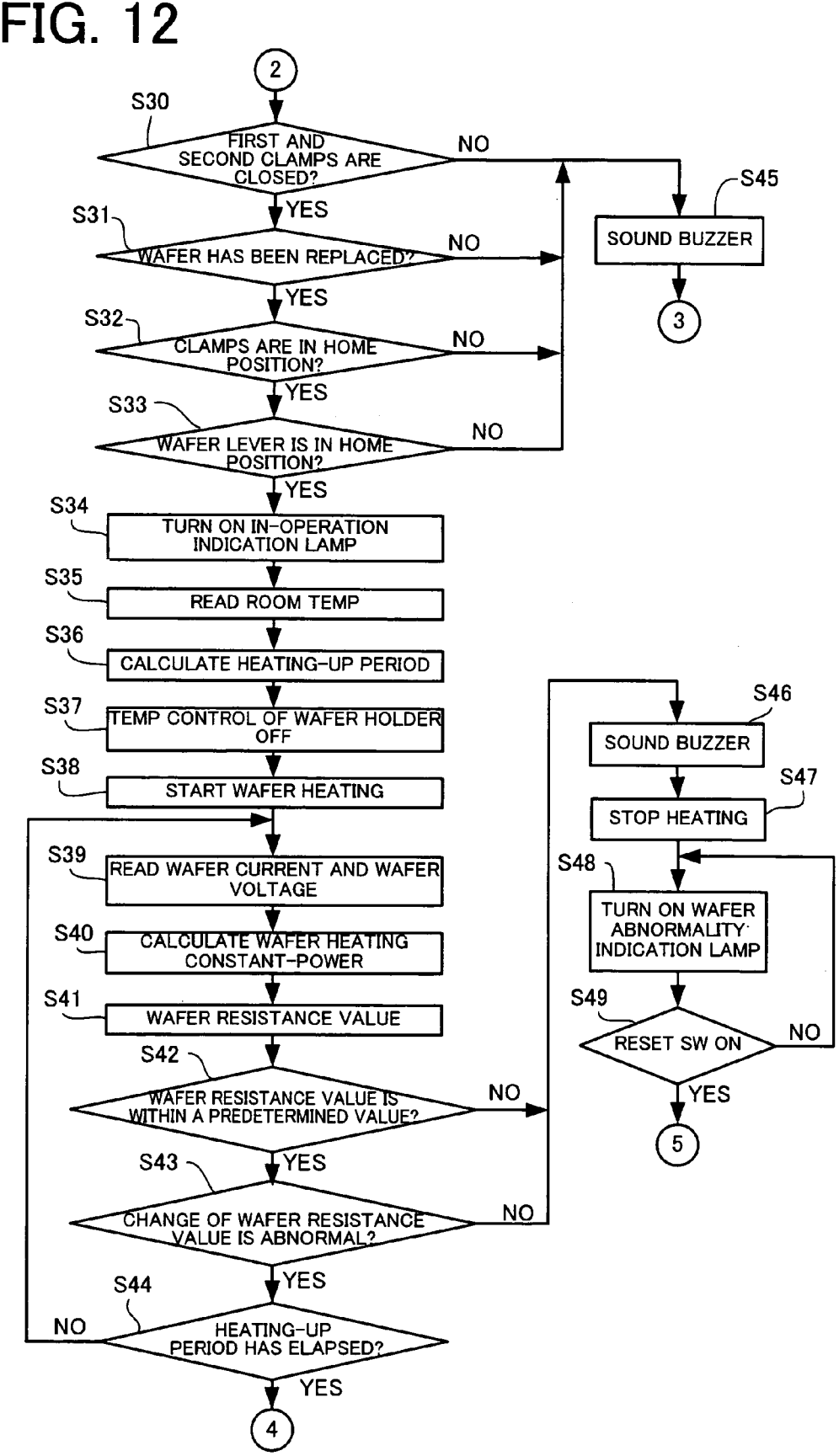
FIG. 12 is also a flowchart for explaining operations of the tube connecting apparatus in the embodiment.
Figure 13:
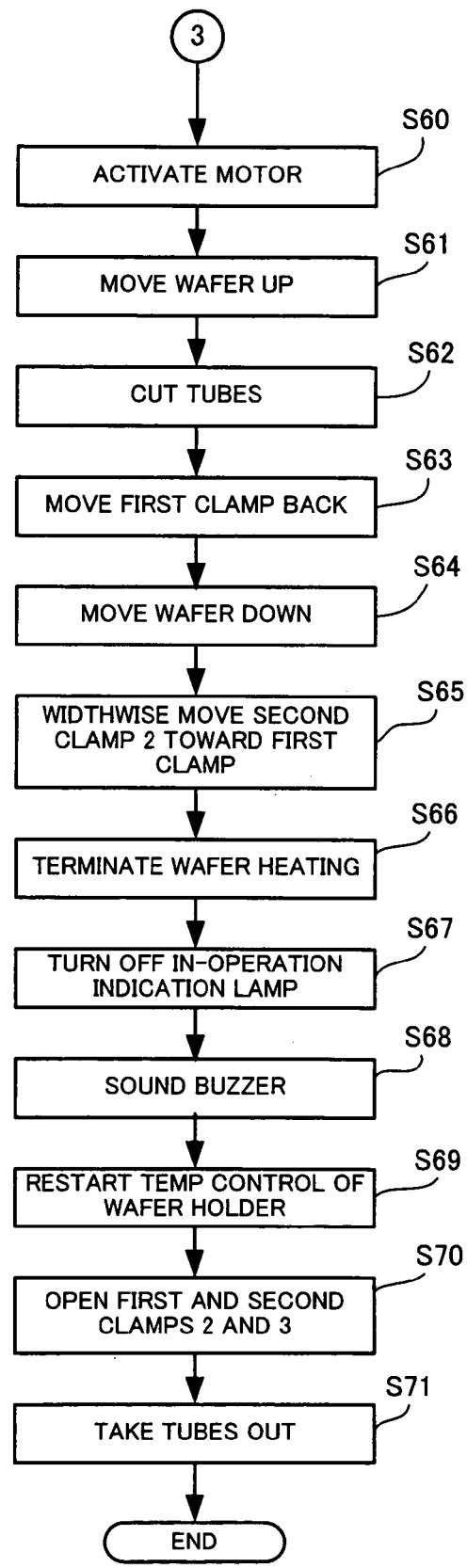
FIG. 13 is also a flowchart for explaining operations of the tube connecting apparatus in the embodiment.

Operations of the tube connecting apparatus 1 having the above structure are described below with reference to the flowcharts in FIGS. 11 through 13. As shown in the flowchart in FIG. 11, first, a power switch 51 provided in the panel 50 in FIG. 9 is pressed (S1). This causes the CPU section 44 to determine as to whether or not the tube connecting apparatus 1 has an abnormal condition (specifically, whether or not an internal connector is disconnected, a heater or others contain broken wires, an internal constant-voltage source is defective, etc.) (S2). If no abnormal condition is detected (S2: YES), the temperature control of the wafer holder 5a is started (S3). Specifically, the wafer holder 5a is heated by the heater 70 and the heater heating control device 69 executes the temperature control based on the output signal from the thermister 71 so that the temperature of the wafer holder 5a reaches a predetermined temperature. The predetermined temperature is preferably set in a range of about 50–80° C., more preferably, about 60–70° C. This is because, as the heating temperature of the wafer holder 5a is low, the heating-up period of the wafer 6 becomes long, and, as the heating temperature of the wafer holder 5a increases excessively, it may affect on peripheral components or there is a risk of a skin burn in case an operator touches the wafer holder 5a. Setting the temperature within the above range makes it possible to shorten the heating-up period of the wafer 6 and to perform stable and accurate control of the temperature of the wafer 6. In the present embodiment, the temperature is set at 65° C. In case the tube connecting apparatus has an abnormal condition (S2: NO), on the other hand, the buzzer sounds (S14).

Subsequently, a clamp reset switch 53 provided on the panel 50 in FIG. 9 is pressed (S4). Then, the CPU section 44 determines as to whether or not the first and second clamps are opened (S5), whether or not the first and second clamps are in the home positions (S6), and whether or not the wafer replacement lever is in the home position (S7). In the tube connecting apparatus 1, as mentioned above, the first clamp 3 has the projection 3i projecting toward the second clamp and the second clamp 2 has the recess 2i which receives the projection 3i. The clamps are arranged such that the second clamp 2 cannot be closed until the first clamp 3 is closed. Thus, the open state of the first and second clamps 3 and 2 is detected by the lever 16 which makes contact with the second clamp 2? and the microswitch 13 which is turned ON/OFF by the lever 16 at the time when the second clamp 2 is closed.

To be more specific, the microswitch 13 is in an OFF state while the second clamp 2 is released. When the second clamp 2 is closed, coming into contact with the lever 16 which moves to turn the microswitch 13 to an ON state. An ON/OFF signal of the microswitch 13 is inputted to the CPU section 44 through the sensor input section 63. When the first and second clamps 3 and 2 are not in the home positions, it is determined by the microswitches 73 and 74 which detect the grooves circumferentially provided on the respective cams. When the wafer replacement lever 22 is in the home position, it is detected by the microswitch 14. When the lever 22 is in the home position, the microswitch 14 is ON. When the lever 22 is not in the home position, the microswitch 14 is OFF. An ON/OFF signal of the microswitch 14 is inputted to the CPU section 44 through the sensor input circuit 63.

If the determinations in S5 to S7 are all YES, the motor is activated, causing the first and second clamps 3 and 2 to return to the home positions (S8). If any one of the determinations in S5–S7 is No, the buzzer sounds (S15), the abnormality indication lamp is turned on (S16), manual release is performed (S17), the reset switch is pressed (S18) to turn off the abnormality indication lamp (S19).

Subsequently, after the first and second clamps 3 and 2 reach the home positions, the two flexible tubes 48 and 49 are set in the first and second clamps 3 and 2 (S9). The first and second clamps 3 and 2 at this time are both in the opened state as shown in FIG. 5 and in the facing state where respective slots 3e and 2e face each other and slots 3f and 2f face each other. The tube 49 in use is set in the slots 3f and 2f on the front side and the new tube 48 to be connected is set in the slots 3e and 2e on the back side.

Figure 18:
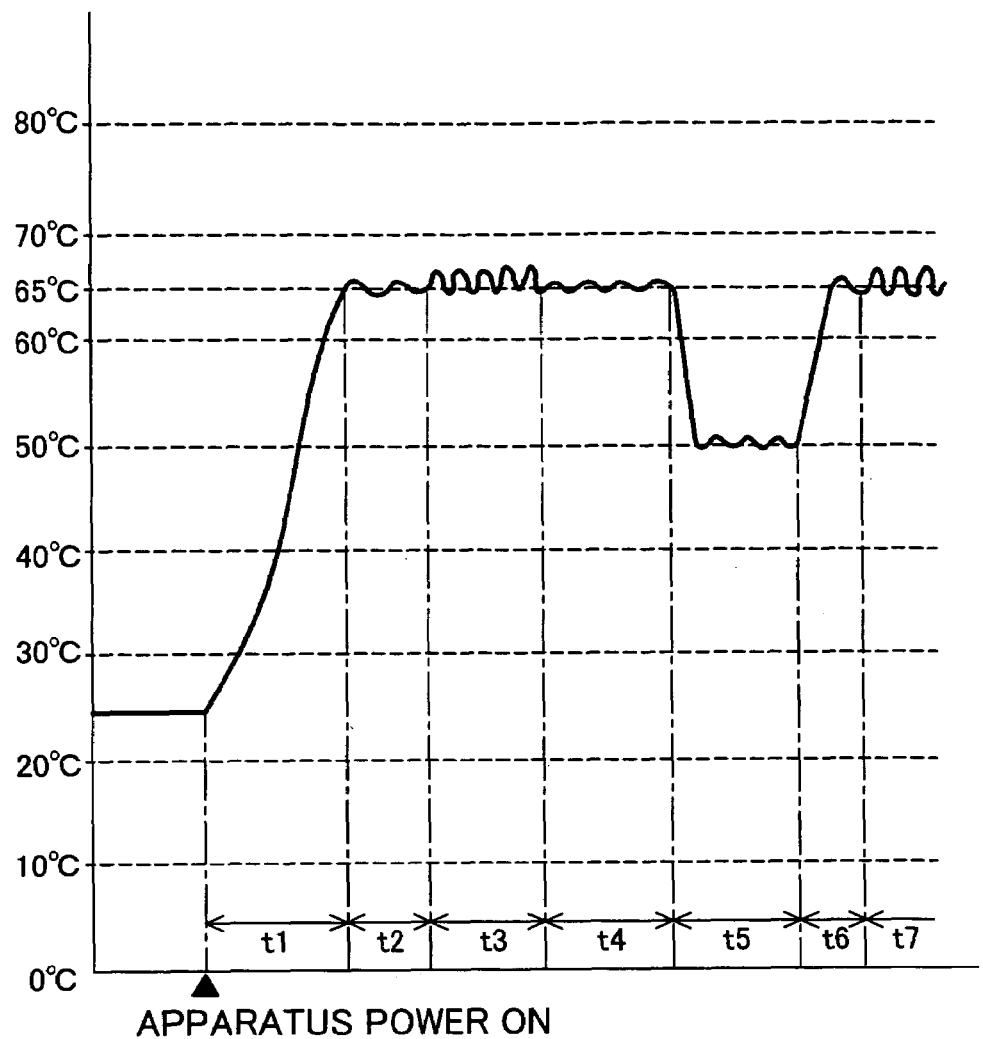
FIG. 18 is a timing chart showing changes in temperature of a wafer holder.

After the first and second clamps 3 and 2 are closed in the above mentioned manner, the wafer replacement lever 22 is pressed toward the clamp to replace the wafer (S10). When the wafer replacement lever 22 is moved toward the clamp, an unused wafer is take out from the wafer cartridge 8, this unused wafer pushes a standby wafer set in the wafer holder 5a, and the standby wafer pushes the used wafer set in the wafer holder 5a. The standby wafer is set in a using position while the used wafer is received in the used-wafer storage box 29 (S11). Upon completion of replacement of wafers, it is checked whether or not the temperature of the wafer holder 5a is a setting temperature (S12). If the temperature of the wafer holder 5a is not the setting temperature (S12: NO), a standby state is established until the temperature of the wafer holder 5a reaches the setting temperature (a period t1 shown in FIG. 18).

If the temperature of the wafer holder 5a is the setting temperature (S12: YES), the tube connecting apparatus 1 is a ready state for connecting (a period t2 shown in FIG. 18). When the start switch 52 on the panel 50 is then pressed (S13), the flow advances to ② in FIG. 12. The CPU section 44 in FIG. 9 determines whether or not the first and second clamps 3 and 2 are closed (S30), whether or not the wafer has been replaced (S31), whether or not the first and second clamps 3 and 2 are in the home positions (S32), and whether or not the wafer replacement lever 22 is in the home position (S33).

Whether or not the first and second clamps 3 and 2 are closed is herein detected by the lever 16 which makes contact with the second clamp 2 when closed and the microswitch 13 which is turned ON/OFF by the lever 16. To be more specific, the microswitch 13 is OFF while the second clamp 2 is in a released state. When closed, the second clamp 2 makes contact with the lever 16 which is moved to turn the microswitch 13 to an ON state. An ON/OFF signal of this microswitch 13 is inputted to the CPU section 44 through the sensor input circuit 63. When the wafer replacement lever 22 is moved toward the clamp for performing the wafer replacement work, the replacement lever 22 turns the microswitch 15 to an ON state one time. Accordingly, whether or not the wafer has been replaced is detected based on an ON signal from the microswitch 15. The ON/OFF signal from the microswitch 15 is inputted to the CPU section 44 through the sensor input circuit 63.

Whether or not the first and second clamps 3 and 2 are in the home positions is detected by the microswitches 73 and 74 as mentioned above.

Figure 11:
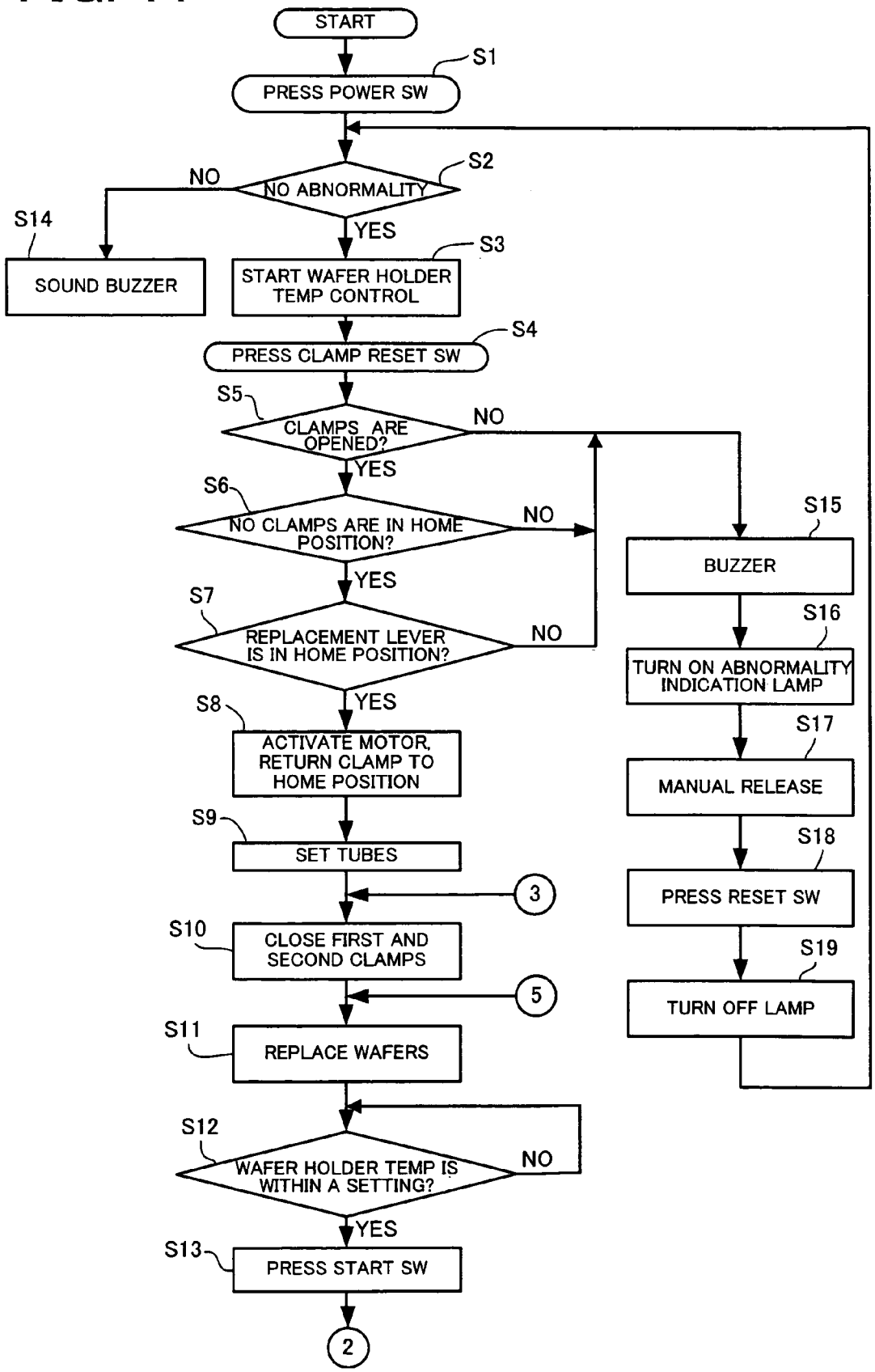
FIG. 11 is a flowchart for explaining operations of the tube connecting apparatus in the embodiment.

If any one determination in S30 to S33 is NO, the buzzer sounds (S45) and the flow returns to ③ in FIG. 11. If all determinations in S30 to S33 are YES, on the other hand, the in-operation indication lamp 47 is turned on (S34). Then, the room temperature is measured by the room-temperature reading sensor 64 and read into the wafer heating control device 68 (S35). The wafer heating control device 68 calculates the heating-up period of the wafer 6 based on the read room temperature (S36). After that, the temperature control of the wafer holder 5a is turned OFF (S37) and the heating of the wafer 6 is started (S38). After the start of heating the wafer 6, the wafer heating control device 68 reads wafer current and wafer voltage (S39) to calculate constant electric power needed for heating the wafer (S40). Based on the calculation result, the PWM control output section 65 for wafer temperature control outputs a PWM signal. The constant-voltage direct-current source 40a is controlled based on the PWM signal to heat the wafer 6.

Subsequently, a resistance value of the wafer 6 is calculated (S41), and it is determined whether the resistance value is within a predetermined value (S42) and whether a change in the resistance value is abnormal (S43). This is done to electrically determine the abnormal condition of the wafer 6. If the resistance value is not within the predetermined value (S42: NO) and if the change in the resistance value is abnormal (S43: NO), the buzzer sounds (S46), the heating of the wafer 6 is stopped (S47), a wafer-abnormality indication lamp is turned on (S48). When the reset switch is pressed (S49), the flow moves to ⑤ in FIG. 11. If the resistance value is within the predetermined value (S42: YES) and further if the resistance value is not abnormal (S43: YES), the heating of the wafer 6 is continued.

For preventing excessive heating of the wafer 6, it is determined whether the heating-up period of the wafer 6 has elapsed (S44). If not elapsed (S44: NO), the above steps are repeated. When the heating-up period has elapsed (S44: YES), the temperature of the wafer 6 is supposed to have reached a predetermined temperature. (about 320° C.) and the flow moves to ④ in FIG. 13 where the motor 42 is activated (S60). This causes the gear 30, gear 31, cams 19 and 17 to rotate, thereby moving the cutting device 5 (the wafer 6) up (S61) to cut the tubes (S62), moving the first clamp 3 back (S63), moving the cutting device (the wafer 6) down (S64), and moving the second clamp 2 widthwise toward the first clamp 3 (S65).

Figure 14:
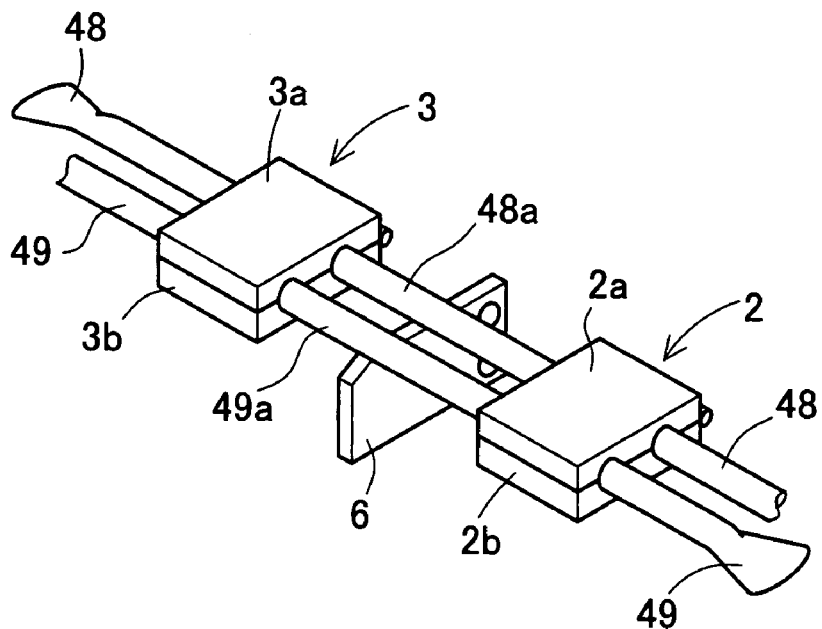
FIG. 14 is an explanatory view for operations of the tube connecting apparatus in the embodiment.
Figure 15:
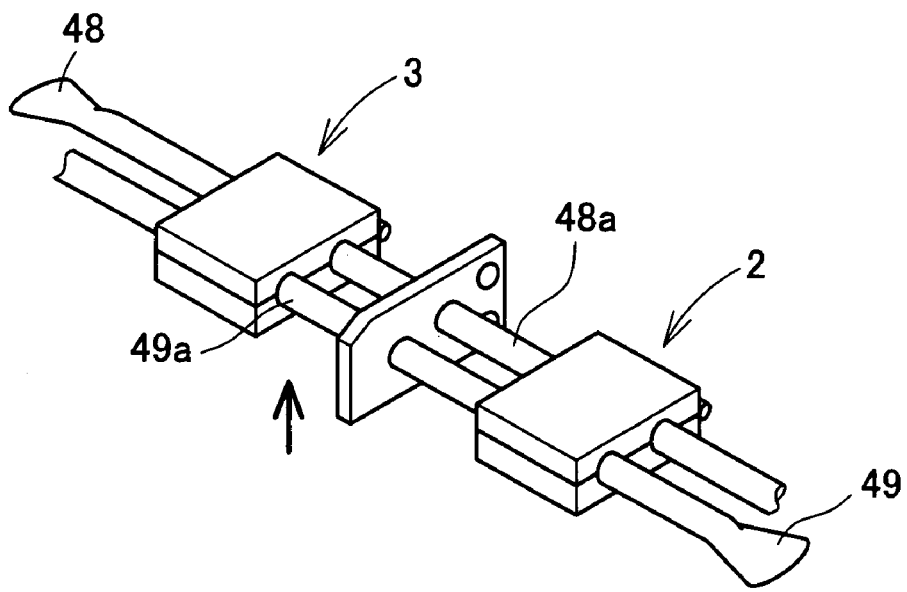
FIG. 15 is also an explanatory view for operations of the tube connecting apparatus in the embodiment.

To be more specific, firstly, as the cam 17 rotates in a direction indicated by an arrow, the follower 5b of the cutting device 5 slides in the cam groove 17a. An initial state where an original point O of the cam groove 17a shown in FIG. 8 is in contact with the follower 5b changes to a state where a point A of the cam groove 17a makes contact with the follower 5b. During a period from the state where the point A of the cam groove 17a shown in FIG. 8 is in contact with the follower 5b to the state where a point B of the cam groove 17a makes contact with the follower 5b, the cutting device 5 is smoothly moved up. During this time, the two flexible tubes are cut. Referring to FIGS. 14 and 15, the two tubes 48 and 49 are held in the first and second clamps 3 and 2, forming tube portions 48a and 49a between the first and second clamps 3 and 2, under which the wafer 6 of the cutting device is placed. As mentioned above, when the rotation of the cam 17 causes the cutting device 5 (the wafer 6) to move up, melting and cutting the two tubes at the tube portions 48a and 49b placed between the first and second clamps 3 and 2 as shown in FIG. 15.

During a period from the state where the point B of the cam groove 17a shown in FIG. 8 makes contact with the follower 5b to the state where a point C of the cam groove 17a makes contact with the follower 5b, as shown in FIG. 8, the wafer 6 is held in the up position, sufficiently melting each cut end of the tubes 48a and 49a. While the state where the point C of the cam groove 17a shown in FIG. 8 makes contact with the follower 5b is changed to the state where a point E of the cam groove 17a makes contact with the follower 5b, the wafer 6 is smoothly moved down. As shown in FIG. 6, when the cam 19 rotates in a direction indicated by an arrow, the follower 18a provided in the arm 18 for moving the first clamp 3 slides in the cam groove 19a. The initial state where an original point O of the cam groove shown in FIG. 6 is in contact with the follower 18a changes to a state where a point F of the cam groove 19a shown in FIG. 6 makes contact with the follower 18a. In other words, the follower 18a makes contact with the point F of the cam groove 19a before the follower 5b of the cutting device 5 makes contact with the point B of the cam groove 17a.

Figure 16:
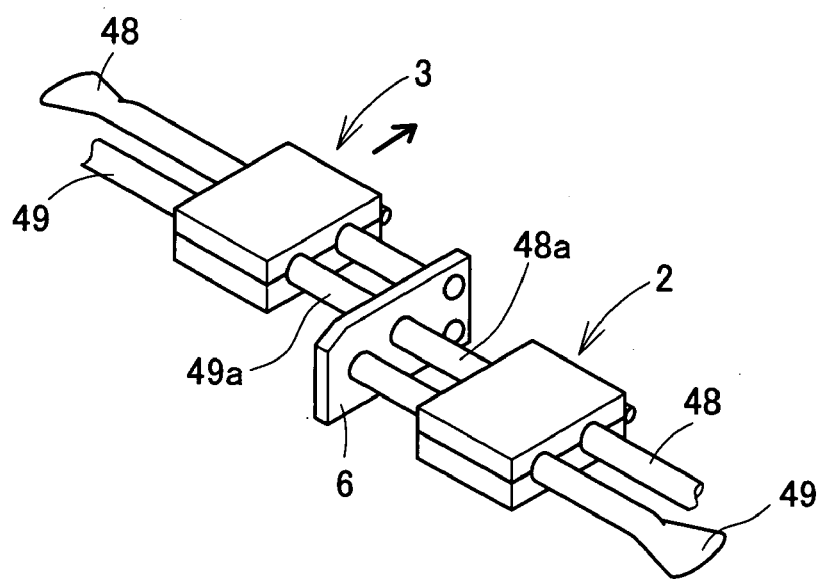
FIG. 16 is also an explanatory view for operations of the tube connecting apparatus in the embodiment.

As shown in FIG. 6, while the state where the point F of the cam groove 19a makes contact with the follower 18a changes to the state where a point G of the cam groove 19a makes contact with the follower 18a, the first clamp 3 is gradually retracted to a state shown in FIG. 16 where the tube portions 49a and 48a to be connected face each other through the wafer 6. This state is maintained during a period from the state where the point G of the cam groove 19a makes contact with the follower 18a changes to the state where the point C of the cam groove 17a makes contact with the follower 5b. The first clamp 3 is held in the position shown in FIG. 16 during a period from the state the point G makes contact with the follower 18a changes to the state where a point H of the cam groove 19a makes contact with the follower 18a. While the state where the point C of the cam groove 18a shown in FIG. 8 makes contact with the follower 5b changes to the state where the point E of the cam groove 17a makes contact with the follower 5b, as described above, the cutting device 5 is smoothly moved down to bring the tube end portions 48a and 49a to be connected into contact with each other.

Upon completion of the downward moving of the wafer 6, i.e., at about the same time when the point E of the cam groove 17a makes contact with the follower 5b, the second clamp 2 is moved widthwise toward the first clamp 3 as shown in FIG. 4. To be more specific, as shown in FIG. 4, the state where a point M of the left side face 17d of the cam groove 17c makes contact with the follower 20 for driving the second clamp 2 changes to the state where a point L of the left side face makes contact with the follower 20, the second clamp 2 is gradually moved toward the first clamp 3. While the state where the point L of the recess 17d of the cam groove 17c makes contact with the follower 20 changes to the state where a point K of the recess 17d makes contact with the follower 20, the second clamp 2 is maintained in the widthwise moved state. By this widthwise moving, the tube portions 48a and 49a are surely brought into close contact with each other, ensuring the connecting therebetween. While the state where the point K of the recess 17d of the cam groove 17c changes to the state where a point J of the left side face 17f makes contact with the follower 20, the second clamp 2 is moved away from the first clamp 3. In this state, the activation of the motor 42 is stopped.

Figure 17:
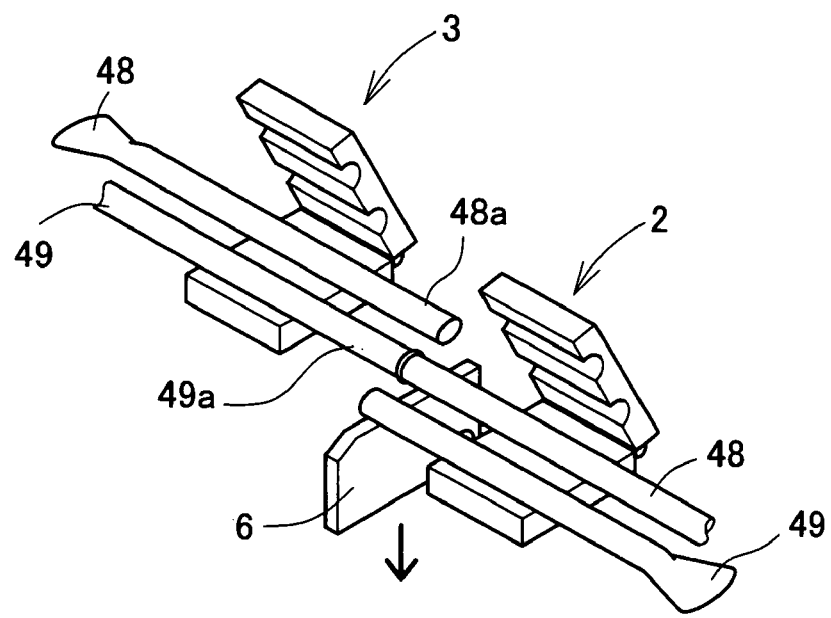
FIG. 17 is also an explanatory view for operations of the tube connecting apparatus in the embodiment.

Hence, the positions of the first clamp 3 and the second clamp 2 are misaligned as shown in FIG. 17, similarly in FIG. 16. As shown in the flowchart in FIG. 13, then, the heating of the wafer 6 is terminated (S66), the in-operation indication lamp is turned off (S67) and the buzzer sounds (S68). The temperature control of the wafer holder 5a is restarted (S69). Thereafter, as shown in FIG. 17, the first clamp 3 and the second clamp 2 are opened (S70), and the tubes are taken out (S71). The tube connecting work is thus completed.

If the tube connecting apparatus 1 is not activated (for example, if an ON/OFF signal is not inputted to the sensor input circuit 63 for a fixed period of time) (a period t4 shown in FIG. 18), the temperature control of the wafer holder 5a is placed in a standby state and the wafer holder 5a is set at 50° C. (a period t5 shown in FIG. 18). This can reduce power consumption. When the tube connecting apparatus 1 is activated again, releasing the standby state (a period t6 shown in FIG. 18), the control temperature is changed to 65° C., executing the normal temperature control (a period t7 shown in FIG. 18). Thus, the power consumption of the tube connecting apparatus 1 can be reduced. Even when the tube connecting apparatus 1 is activated for successive tube connecting operations, the wafer holder 5a is maintained at about 65° C. (a period t3 shown in FIG. 18). Accordingly, the thermal flux from the wafer holder 5a to the wafer 6 at the start of heating the wafer 6 remains constant, so that the temperature control of the wafer 6 can be performed stably and accurately.

According to the tube connecting apparatus 1 in the present embodiment, as explained in detail, the wafer holder 5a is heated in advance to about 65° C. by the heater 70 and then the heating control of the wafer 6 is performed through the constant power control. This makes it possible to shorten the heating-up period of the wafer 6 and achieve stable and accurate temperature control of the wafer 6. Since there is no need for detecting the temperature of the wafer 6, it is possible to eliminate the use of the wafer temperature detecting means for detecting the temperature of wafer. Accordingly, the adjustment work of the wafer temperature detecting means in mounting it becomes unnecessary, resulting in an improved production efficiency.

The above mentioned embodiment is merely an example, which is not limited the present invention thereto. The present invention may be embodied in other specific forms without departing from the essential characteristics thereof.

INDUSTRIAL APPLICABILITY

In the tube connecting apparatus of the invention, as described above, the heating control means controls the heating means to heat the wafer holder to the predetermined temperature. Before the wafer is heated, the wafer holder is maintained at the predetermined temperature. Thus, the temperature of the wafer holder is continuously constant at the start of heating the wafer, that is, the thermal flux from the wafer holder to the wafer is always constant. This makes it possible to stably, accurately perform the temperature control of the wafer by the wafer heating control means. Since the wafer holder is maintained at the predetermined temperature, the time needed for heating the wafer to the predetermined temperature can be shortened.

In the tube connecting apparatus according to the invention, the temperature control of the wafer is performed through constant power control of the heating means. The use of the wafer temperature detecting means for detecting the temperature of the wafer can be eliminated. Accordingly, the adjustment work of the wafer temperature detecting means in mounting it becomes unnecessary, resulting in an improved production efficiency.

Furthermore, in the tube connecting apparatus according to the invention, the heating control means controls the temperature of the wafer holder within a range of 50 to 80° C. before the wafer is heated by the wafer heating means. The heating-up period of the wafer can be shortened and the wafer temperature control can be performed stably and accurately. The temperature of the wafer holder will not excessively increase, with the result that peripheral components are not affected and no risk of a skin burn is caused in case an operator touches the wafer holder.

The invention claimed is:

1. A tube connecting apparatus for connecting flexible tubes in sterile condition, the apparatus comprising:
   a first clamp and a second clamp which hold at least two flexible tubes;
   cutting means for cutting the flexible tubes between the first and second clamps; and
   moving means which moves at least one of the first clamp and the second clamp so that the end portions to be connected of the flexible tubes cut by the cutting means contact closely with each other;
   wherein the cutting means comprises:
      a wafer for melting and cutting the flexible tubes;
      a wafer holder which holds the wafer;
      heating means for heating the wafer holder;
      temperature detecting means for detecting the temperature of the wafer holder; and
      heating control means for controlling the heating means; and
   the heating control means controls the heating means so that the wafer holder is heated to a predetermined temperature based on output of the temperature detecting means.

2. A tube connecting apparatus for connecting flexible tubes in sterile condition, the apparatus comprising:
   a first clamp and a second clamp which hold at least two flexible tubes;
   cutting means for cutting the flexible tubes between the first and second clamps; and
   moving means which moves at least one of the first clamp and the second clamp so that the end portions to be connected of the flexible tubes cut by the cutting means contact closely with each other;
   wherein the cutting means comprises:
      a wafer for melting and cutting the flexible tubes;
      wafer heating means for heating the wafer;
      wafer heating control means for controlling the wafer heating means;
      a wafer holder which holds the wafer;
      heating means for heating the wafer holder;
      temperature detecting means for detecting the temperature of the wafer holder; and
      heating control means for controlling the heating means; and
   the heating control means controls the heating means before the wafer is heated by the wafer heating means so that the wafer holder is heated to a predetermined temperature based on output of the temperature detecting means.

3. The tube connecting apparatus according to claim 1, wherein
   the predetermined temperature is within 50 to 80° C.

4. The tube connecting apparatus according to claim 1, wherein the heating control means controls the heating means so that the temperature of the wafer holder is lower than the predetermined temperature when a subsequent tube connecting operation is not conducted for a predetermined period of time after a tube connecting operation.

5. The tube connecting apparatus according to claim 1, wherein
the temperature detecting means includes a thermister and a temperature reading circuit which measures the temperature of the wafer holder based on an output signal of the thermister.

6. The tube connecting apparatus according to claim 2, wherein
the wafer heating control means controls the wafer heating means through constant power control based on a level of electric current and voltage of the wafer.

7. The tube connecting apparatus according to claim 2, wherein
the wafer heating control means controls the wafer heating means through pulse width modulation control based on a difference between an amount of electric power consumption of the wafer calculated based on the levels of electric current and voltage of the wafer and an amount of target electric power set in advance.

8. The tube connecting apparatus according to claim 2, wherein
the predetermined temperature is within 50 to 80° C.

9. The tube connecting apparatus according to claim 2, wherein
the heating control means controls the heating means so that the temperature of the wafer holder is lower than the predetermined temperature when a subsequent tube connecting operation is not conducted for a predetermined period of time after a tube connecting operation.

10. The tube connecting apparatus according to claim 2, wherein
the temperature detecting means includes a thermister and a temperature reading circuit which measures the temperature of the wafer holder based on an output signal of the thermister.

* * * * *